United States Patent [19]

Drocourt et al.

[11] Patent Number: 5,751,839
[45] Date of Patent: *May 12, 1998

[54] APPARATUS AND PROCESS FOR THE DETECTION AND COUNTING OF RARELY OCCURRING MAMMALIAN CELLS

[75] Inventors: Jean-Louis Drocourt, Yerres; Jean-Gérard Guillet, Vanves, both of France; Warren Groner, Great-Neck, N.Y.

[73] Assignee: Chemunex, Maisons-Alfort, France

[*] Notice: The term of this patent shall not extend beyond the expiration date of Pat. No. 5,663,057.

[21] Appl. No.: 492,762

[22] Filed: Jun. 21, 1995

[30] Foreign Application Priority Data

Nov. 17, 1994 [EP] European Pat. Off. ........... 94402609.5

[51] Int. Cl.⁶ ................................ G06K 9/00; G06K 9/46
[52] U.S. Cl. ........................ 382/133; 250/461.2; 356/39; 377/10
[58] Field of Search ..................... 250/361, 453.11, 250/454.11, 458.1, 459.1, 461.1, 461.2, 462.1, 360.1; 356/39, 335, 336, 337, 338, 343, 432, 434, 438–444; 364/413.07, 413.08, 413.1, 556; 382/133, 134, 278, 318, 319; 348/79, 95, 202

[56] References Cited

U.S. PATENT DOCUMENTS

| | | | |
|---|---|---|---|
| 4,180,831 | 12/1979 | Morton et al. | 358/160 |
| 4,647,531 | 3/1987 | Kamentsky | 435/7 |
| 5,037,207 | 8/1991 | Tomei et al. | 250/458.1 |
| 5,093,866 | 3/1992 | Douglas-Hamilton et al. | 382/6 |
| 5,103,101 | 4/1992 | Berglund et al. | 250/492.2 |
| 5,523,207 | 6/1996 | Kamentsky et al. | 435/6 |
| 5,578,832 | 11/1996 | Trulson et al. | 250/458.1 |

OTHER PUBLICATIONS

High–Speed Video Imaging and Digital Analysis of Microscopic Features in Contracting Striated Muscle Cells. Kenneth Roos and Stuart Taylor, Optical Engineering, Feb. 1993, vol. 32 No. 2 pp. 306–313.

Primary Examiner—Joseph Mancuso
Assistant Examiner—Marc Bobys
Attorney, Agent, or Firm—Oblon, Spivak, McClelland, Maier & Neustadt, P.C.

[57] ABSTRACT

Apparatus and process capable of rapid detection and counting of rarely occuring mammalian cells in blood and other tissues which have been labeled with a fluorescent dye.

The process includes: scanning a solid support on which a specimen potentially containing fluorescent cells has been deposited, with an incident beam from a laser, forming a laser spot on the solid support, the laser spot being substantially greater than the cells to be detected, the laser spot size being between 15 and 30 μm; and simultaneously: detecting the resultant fluorescent light at least at one wavelength; establishing a set of correlated-features by a line-to-line correlation of individual features; comparing the correlated-features on each pair of adjacent lines in time synchrony, at least at two different wavelengths $\lambda_1$ and $\lambda_2$; making a size discrimination of retained events and selecting those having a size corresponding to the type of cells searched; determining if, for retained events after size discrimination, the events energy profile in three dimensions is within predetermined Gaussian shape criteria; and counting the remaining events to determine and to count exclusively the fluorescent cells present on the solid support.

10 Claims, 9 Drawing Sheets

APPARATUS AND PROCESS FOR THE DETECTION AND COUNTING OF RARELY OCCURRING MAMMALIAN CELLS

FIELD OF THE INVENTION

The present invention relates to an apparatus and a process capable of rapid detection and counting of rarely occuring mammalian cells in blood and other tissues which have been labeled with a fluorescent dye.

BACKGROUND OF THE INVENTION

The automated detection of small quantities of molecules or cells which have been labeled with a fluorescent dye is a well understood and often practiced element of diagnostic medicine. Traditionally, the detection and quantification follows one of three general forms:

- in the first form ("solution chemistry"), the molecules are detected after they are released from the cells that carry them and the resulting fluorescent intensity is related to the molecular concentration.
- in the second form (flow cytometry) intact cells are caused to flow past a sensitive fluorescent detection station after labeling with a fluorescent dye. The labeled cells are then counted as a fraction of the total cells.
- in the third form (image analysis) the labeled tissue is presented to an automated microscope on a solid substrate and the cells are detected and counted through an analysis of the image formed by the microscope. Typically, the image is scanned with a small laser spot to excite the fluorescent molecules.

In each of these forms, there is a significant limitation in the sensitivity which effects their application to the detection of rare events. This limitation may be particularly severe in the practical application of the modern technology of molecular diagnostics.

It is increasingly necessary in biological or anatomopathological research or routine diagnostics analysis to detect a small number of abnormal cells among a large number of normal cells. Such examples of abnormal cells are tumor cells or cells which have been infected by a virus. Such abnormal cells can be identified by a fluorescent label which addresses either a component of the cells, such a specific protein or genes through techniques such as hybridization in situ, PCR in situ.

In many medical situations, it would be of great benefit to detect and count accurately and rapidly, on a large number of speciman, a very low number of abnormal cells in each sample. For example, an early detection of a few tumor cells in a biopsy may permit an intervention before the dissemination of tumor cells and prevent extension of the cancer tumor.

Another example relates to the early detection and monotoring of the number of cells penetrated by an invading virus (such as HIV). An early detection may help preventing contamination of other persons, and a close monitoring may be very valuable for the treatment of the disease.

For this type of application, the sensitivity of detection must be very high as it is important to detect one single abnormal cell among more than $10^5$ other cells.

In order to get statistically valid information, it is in some respect desirable to count around 100 abnormal cells, which means examining other $10^7$ total cells.

The visual examination of the sample spread over a solid support with a microscope is a tedious process, very time consuming. It is complicated by the presence of other fluorescent material. When searching anormal cells with a microscope, a large surface has to be viewed, and the risk of missing one abnormal cell is high.

The utilisation of confocal microscopy or image analysis permits the detection of the abnormal cells (rare events). However, in practical applications, the scanning is slow and the area analysed is small.

Indeed, the principal technological issues in detecting rare cells such as those occuring in the examples cited above with either flow cytometry or image analysis are illustrated by considering the detection signal to noise ratio, or more specifically the probability that a false signal will be detected. It is well known that the probability of a false signal will increase linearly with the amount of time that the detector is required to look for the rare event. Thus, to maintain the same ability to discriminate between false and true signals, the required ratio of signals to noise must increase as the probability of a true signal decreases. Alternatively, for a given signal to noise ratio, there is a limit in terms of the frequency of occurrence below which an event cannot be reliably detected.

There is one means of overcoming the limitation cited above which is only applicable to the third form of analysis (image analysis). In this form since the cells are fixed to a solid support it is possible to reanalyze the specimens and discriminate against false signals in the second analysis. Thus, one means which is well known of improving the rare event detection capability of an automated microscope is to first analyze the specimen in a coarse fashion and then return in a second pass to examine in more detail the suspected positive signals. However, this technique is still limited in the speed in which the analysis is made. This limitation results from the fact that the probability of detection must be maintained in the first coarse scan. Thus, in fluorescent detection the illuminating spot size must remain small enough to achieve sufficient intensity, and the scan must be slow enough to enable a positive recognition of the rare event on the first pass.

In order to better understand this problem, it is useful to note that in electronic imaging systems the resultant image is made up of individual picture elements (pixels). In the current state of the art of electronic imaging, even the best video cameras can only form images of as many as 100,000 or 1 million pixels. However, the diameter of a single cell is typically in the order of 10 μm while the surface of the solid support to review is in the order of 5 cm². Thus, if we consider one pixel to be the size of a cell, it would take around 30 million pixels to cover the entire support.

As a result either a single picture element (pixel) must be made much larger than the dimensions of a single cell or the analysis must include many sequential images. However, neither of these approaches is satisfactory. In the first case, the sensitivity of detection is lowered while, in the second case the time and complexity of analysis are limiting factors.

As a consequence, in actual practice, a small area of the sample spread over the solid support is analysed by this technique, which may be acceptable for research purposes but is not acceptable for routine in vitro diagnostic testing in view of potential false negative results, with severe medical applications.

Another limitation of this technique is in the data processing. Since, in the case of two scans, the positive event is only confirmed after completion of the second analysis, the data processing apparatus must maintain a complete record of the first analysis. In rare event detection the occurrence of a positive element is so infrequent that data from more than a million negative elements may have to be stored for each positive event.

In addition, the labelling of the searched cells may be fragile and rapidly decreasing with time, with the result that a second scanning may lead to false negative results.

Lastly, the technique does not lend itself easily to the development of appropriate procedures to automatically discriminate the fluorescent cells searched from the various particles present on the sample which are either autofluorescent or made fluorescent by adsorption of the dye. Indeed, the size and shape of the abnormal cell to detect can vary substantially, making a comparison to a model quite questionable.

SUMMARY OF THE INVENTION

The present invention relates to an apparatus and a process capable of rapid and accurate detection and count of rare mammalian cells made fluorescent and present on a solid support, by a laser scanning of the said solid support. The limitations cited above are overcome by using at least a scanning spot larger than the cells to be detected, preferably an elongated spot, together with an overlapping scanning pattern.

Furthermore, through the use of this unique apparatus, a rapid scan of a relatively large solid support (typically a few square centimeters) is accomplished in such a way that no rare mammalian cell to detect is missed and with close to real time rejection of false signals. A discrimination process (the discriminator) ensures the automatic and fast separation of fluorescent signals emitted by searched cells, from fluorescent signals emitted by autofluorescent particles, or other material which may have been made fluorescent.

In order to understand the invention it is instructive to note that it is known that the probability of detection for independent scan passes over a target is proportional to the square root of N times the probability of detection for a single pass. It is also known that the probability of detection for a single pass is in turn inversely proportional to the square root speed at which the pass is made. Thus, in general, scanning the field twice, at twice the speed, is equivalent in probability of detection to scanning once and no net gain in scan time is realized. However, if the two passes are added in time synchrony, they are no longer independent trials, and a signal event, (which will be correlated between the two passes), will be favored over a noise event, (which will be uncorrelated). Thus, increasing the probability of detection and permitting a decrease in the scan time.

In the invention, an increased scanning rate is accomplished, for instance, by scanning with a large laser spot (see FIG. 1), and overlapping the scan, such that each element in the field is scanned at least twice.

The results of each adjacent pair of scans in the X direction are then compared in time synchrony for the purpose of maintaining the probability of detection by eliminating uncorrelated signals. Thus, each positive event is correlated between two or more scan lines, (depending on the size of the fluorescent object).

Definitions:

As the laser spot moves along scan lines on the solid support (such as a glass slide) the fluorescence light emitted (if any) is measured continously by one or more detectors (at various wavelengths). The analog signal coming out of the detectors is digitized by taking its value at constant frequency intervals.

Reading: a reading is the value of the signal at the time of measurement.

Sample: a sample is defined as a reading of the signal from the detector which exceeds a given dynamic threshold.

Feature: a set of adjacent samples on one scan line is called a feature.

Line to line correlation: 2 samples are said to be correlated when they appear in time synchrony on two adjacent scan lines.

Single feature: a feature which appears on only one scan line, ie which is not correlated, is called a single feature.

Fluorescent spot : fluorescence emitted by any fluorescent particle when excited by a laser beam. These particles can be cells or other elements such as dust.

The particles can be autofluorescent or have been made fluorescent for the detection (for example, cells).

Event: an event is a set of at least two features which are correlated in time synchrony on adjacent scan lines. An event is the translation of a fluorescent spot in the measurement process.

An event may subsequently be classified by the discriminator as either a positive event (ie an event being searched, such as a cell) or as a noise event (ie an event to be rejected as due to fluorescence generated for example by autofluorescent particles). A noise event, if included in the final count, would give false positives.

Laser spot: light spot formed by a laser beam on a solid support.

Interline or line spacing Y: distance between two scanning lines.

Said definitions are illustrated in FIG. 2, in which samples are represented by o and in which the length of an event (set of correlated features) corresponds to the number of accumulated count of samples from the start of the feature occuring the earliest in a scan-line in the scan direction, and the end of the feature which terminates the latest in a scan line, said counting taking as one sample all the correlated samples on different scan lines, and the width of an event is defined by the number of adjacent lines on which the same event appears.

In one aspect of the present invention, a method for counting fluorescent labelled cells on a solid support such as a glass slide, is provided; said method is characterized in that it comprises:

scanning a solid support on which a specimen potentially containing fluorescent cells has been deposited, with an incident beam from a laser, forming a laser spot on the solid support, said laser spot being substantially greater than the cells to be detected, said laser spot size being comprised between 15 and 30 µm, wherein the distance between two scanning lines is such that each element of the said support is scanned at least twice, by partial overlapping of adjacent scanning paths, and is preferably less than half the dimension of said laser spot size; and simultaneously:

detecting the resultant fluorescent light at least at one wavelength, by selecting only detected signals exceeding a given threshold (=samples), for example a dynamic threshold, wherein a set of adjacent samples on a scan-line represents a feature;

establishing a set of correlated-features by a line-to-line correlation of individual features, by comparing features on each pair of adjacent lines in time-synchrony, counting the number of lines over which said set of correlated-features occur, each set of correlated-features forming an event, and eliminating any single uncorrelated-features (=single feature);

correlation is considered as existing when one or more samples within the two features under comparison are detected in the same position on said pair of line. The number of lines over which said set of correlated-features occur is counted, and thereafter used in size discrimination.

comparing said correlated-features on each pair of adjacent lines in time synchrony, at least at two different wavelengths $\lambda_1$ and $\lambda_2$, for selecting the correlated-features having an emission intensity ratio at said two wavelengths lower than a predetermined number, being specified that if the emission ratio at said wavelengths generated by any correlated samples is greater than a predefined value, the complete event is eliminated;

making a size discrimination of retained events and selecting those having a size corresponding to the type of cells searched;

determining if for retained events after size discrimination, the events energy profile in three dimensions is within predetermined Gaussian shape criteria and rejecting events not within said predetermined Gaussian shape criteria;

such analysis is for instance performed by a software curve-fitting algorithm. All events within the criteria are accepted as fluorescent cells for the final count; those outside the criteria are classified as noise (dust or other particles on said solid support);

counting said remaining events to determine and to count exclusively the fluorescent cells present on said solid support.

More precisely, according to a preferred embodiment of said aspect of the invention, said size discrimination is carried out by:

determining the length of each event by counting the number of samples, by starting with the sample appearing first on the scanning direction on whatever feature of said event occuring the earliest, continue to include the sample appearing last in the scan direction on whatever feature ends last, said counting taking as one sample all the correlated samples on different scan lines, determining the width of said event by counting the number of adjacent lines covered by the same event and eliminating events for which the number of said counted samples is greater than a predetermined number A, and/or the number of said adjacent scan-lines is greater than a predetermined number B.

In another aspect of the present invention, the instant process it characterized in that it comprises:

spreading the specimen to be analyzed and potentially containing the rare mammalian cells to be detected, over a solid support, in such a way to obtain a thin layer;

depositing on the solid support appropriate reagents to fluorescently label the cells searched using techniques such as monoclonal antibodies, in situ hybridisation, in situ PCR, enzyme-linked probes, capable when exited to emit a fluorescent light at a selected wavelength; such techniques being used either individually or simultaneously on a given sample to produce fluorescent light at one or more wavelength as a discrimination tool or as a way of identifying or selecting only certain type of rare cells;

scanning said solid support with an incident beam from a laser, forming a laser spot on said solid support, said laser spot being substantially greater than the cells to be detected, said laser spot size being comprised between 15 and 30 µm, wherein the distance between two scanning lines is such that each element of the said support is scanned at least twice, by partial overlapping of adjacent scanning paths, and is preferably less than half the dimension of said laser spot size; and simultaneously:

detecting the resultant fluorescent light at least at one wavelength, by selecting only detected signals exceeding a given threshold (=samples), wherein a set of adjacent samples on a scan-line represents a feature;

establishing a set of correlated-features by a line-to-line correlation of individual features, by comparing features on each pair of adjacent lines in time-synchrony, counting the number of lines over which said set of correlated-features occur, each set of correlated-features forming an event, and eliminating any single uncorrelated-features (=single feature);

correlation is considered as existing when one or more samples within the two features under comparison are detected in the same position on said pair of line. The number of lines over which said set of correlated-features occur is counted, and thereafter used in size discrimination;

comparing said correlated-features on each pair of adjacent lines in time synchrony, at least at two different wavelengths $\lambda_1$ and $\lambda_2$ for selecting the correlated-features having an emission intensity ratio at said two wavelengths lower than a predetermined number, being specified that if the emission ratio at said wavelengths generated by any correlated samples is greater than a predefined value, the complete event is eliminated;

making a size discrimination of retained events and selecting those having a size corresponding to the type of cells searched;

determining if for retained events after size discrimination, the events energy profile in three dimensions is within predetermined Gaussian shape criteria and rejecting events not within said predetermined Gaussian shape criteria;

such analysis is for instance performed by a software curve-fitting algorithm. All events within the criteria are accepted as fluorescent cells for the final count; those outside the criteria are classified as noise (dust or other particles on said solid support);

counting said remaining events to determine and to count exclusively the fluorescent cells present on said solid support.

As stated hereabove, the distance between two scanning lines (interline or line spacing y) is less than half the dimension of said laser spot size, leading to an overlap of the scanned surface.

More precisely, according to a preferred embodiment of said aspect of the invention, said size discrimination is carried out by:

determining the length of each event by counting the number of samples, by starting with the sample appearing first on the scanning direction on whatever feature of said event occuring the earliest, continue to include the sample appearing last in the scan direction on whatever feature ends last, said counting taking as one sample all the correlated samples on different scan lines, determining the width of said event by counting the number of adjacent lines covered by the same event and eliminating events for which the number of said counted samples is greater than a predetermined number A, and/or the number of said adjacent scan-lines is greater than a predetermined number B.

Preferably, the step of detecting the resulting fluorescent light is performed by measuring signals exceeding a dynamic threshold (=samples), by means of a digital signal processor (DSP).

Said DSP allows to differentiate between wanted signals (corresponding to cells) and unwanted signals (electronic noise, for instance).

Such a process avoids, unexpectedly, both false negative and false positive results.

The hereafter Table I summarizes the potential causes for false negative or false positive results and the relevant steps of the instant process to eliminate the errors.

TABLE I

| | Possible causes | Relevant steps for correction |
|---|---|---|
| False positive | PMT noise<br>Background fluorescence of filter<br>Autofluorescent dirt or particle<br>having absorbed the dye | Line to line correlation<br>Gaussian curve<br>Dynamic thresholding<br>Colour discrimination<br>Size discrimination |
| False negative | Area not covered<br>cell signal not identified above background<br>Cell assigned as PMT noise or dirt | Overlapping and full filter scanning<br>Background level thresholding<br>Colour discrimination<br>Line to line correlation<br>Size discrimination |

It must be highlighted that the present process handles only with fluorescent spots and identifies fluorescently-labeled bacteria by analysis of the label's fluorescent response to a scanning laser. The analysis technique makes use of fluorescence discrimination comprising:

evaluation of the number of samples on a scan line (=feature), line to line correlation and number of correlated features in view to make a "size discrimination" as defined hereabove and to provide an accurate detection of cells.

Therefore, the instant analysis technique makes use of the size of the object to detect in the following two ways:

the fluorescent response on any single scan line must be large enough to exceed a predetermined noise threshold;

a feature must be detected with a predetermined degree of overlap on at least two consecutives line scans.

These requirements mean that the instant process differs markedly from imaging systems, which require significantly more information on the shape and size of a feature.

These requirements drive the design of an imaging system towards small laser spot size, in order that the spot is smaller than the object being detected. The instant spot size can be large relative to the feature, and is currently of the order of 10 times the feature size. This gives major benefits in sampling speed, optical accuracy requirements, and processing power (data handling rate and memory requirements).

Unexpectedly, the instant process provides:

dynamic thresholding of signal level: the data processing system continuously monitors background noise level, and adjusts the threshold level which features must exceed to be regarded as significant. This allows the system to tolerate variation in the behaviour of the glass slide (solid support), both from glass slide to glass slide, and over the area of a single glass slide;

line-to-line correlation of signals: in order to be assigned as cells, features must be present on at least two scan lines;

use of a green fluorescence spectrum shape for feature discrimination (red/green signal level). A feature detected in the green channel must have a corresponding red channel signal small or nil, as predicted from the shape of the green fluorescent marker emission spectrum. A higher level of red channel response will cause the feature to be rejected;

signal discrimination: signals must be present for a predetermined number of scan points in order to be acceptable. Short signals are rejected as noise;

correlated features comprising above a predetermined number of samples or above a predetermined number of lines (i.e., either along a given scan line, or across several line scans) are rejected.

In another aspect of the present invention, an apparatus for detection and counting of cells by fluorescence on a solid support is provided.

Said apparatus comprises:

a laser light source for emitting an incident light beam, cooperating with means for focusing said laser beam into a laser spot, the dimension of which on a solid support is substantially greater than the type of mammalian cells to be detected and counted, said laser spot size being comprised between 15 and 30 µm;

scanning means for directing the light from said light source onto said solid support to spotwise irradiate the mammalian cells to produce fluorescence spots, wherein the distance between two scanning lines is such that each element of the support is scanned at least twice, by partial overlapping of adjacent scanning paths and is preferably less than the dimension of said laser spot size;

means for detecting and photoelectrically converting said emitted fluorescence at least at two different wavelengths $\lambda_1$ and $80_2$;

means for discriminating and eliminating non-mammalian fluorescence including a digital signal processor and a plurality of optic paths for selecting at least two emission fluorescence wavelengths;

signal processing means for establishing sets of correlated-features by a line-to-line correlation of individual features, by comparing features on each pair of adjacent lines in time synchrony, counting the number of lines over which said set of correlated-features occur, each set of correlated-features forming an event, and eliminating any single uncorrelated feature, occuring only on one line; comparing said correlated-features on each pair of adjacent lines in time synchrony, at least at two different wavelengths $\lambda_1$ and $\lambda_2$, for selecting the correlated-features having an emission intensity ratio at said two wavelengths lower than a predetermined number, being specified that if the emission ratio at said wavelengths generated by any correlated features is greater than a predefined value, the complete event is eliminated; making a size discrimination of retained events and selecting the events having a size corresponding to the type of mammalian cells searched; determining if for retained events after size discrimination, the events energy profile in three dimensions is within predetermined Gaussian shape criteria and rejecting events not within said predetermined Gaussian shape criteria, and counting said remaining events to determine and to count exclusively the fluorescent mammalian cells present on said solid support.

Said apparatus allows that the entire surface of the solid support is scanned.

According to one aspect of said apparatus, said scanning means comprises a first oscillating mirror, the axis of oscillation of which is perpendicular to the axis of the light beam for scanning a line by the beam; and a second mirror, the axis of which is perpendicular to the axis of oscillation of the first mirror, said second mirror executing a scanning movement synchronized with the scanning movement of said first mirror.

According to another aspect of the apparatus, said detecting means includes at least two photomultipliers as a means for the photoelectric conversion.

According to another aspect of the apparatus, said laser spot has an elongated shape.

According to another aspect of the apparatus, said solid support is a glass slide.

According to another aspect of the apparatus, said sample holder cooperates with cooling means, such as ones leading to Peltier effect.

In addition, a thin layer of a material such as silicon may be sandwiched between said sample holder and said glass slide.

Said thin layer has, for instance, the following advantages: no autofluorescence, low light reflexion at the excitation wavelength and easy to clean.

The following figures can be used to describe the means by which the invention was reduced to practice.

DESCRIPTION OF THE PREFERRED EMBODIMENTS

Figure 3:
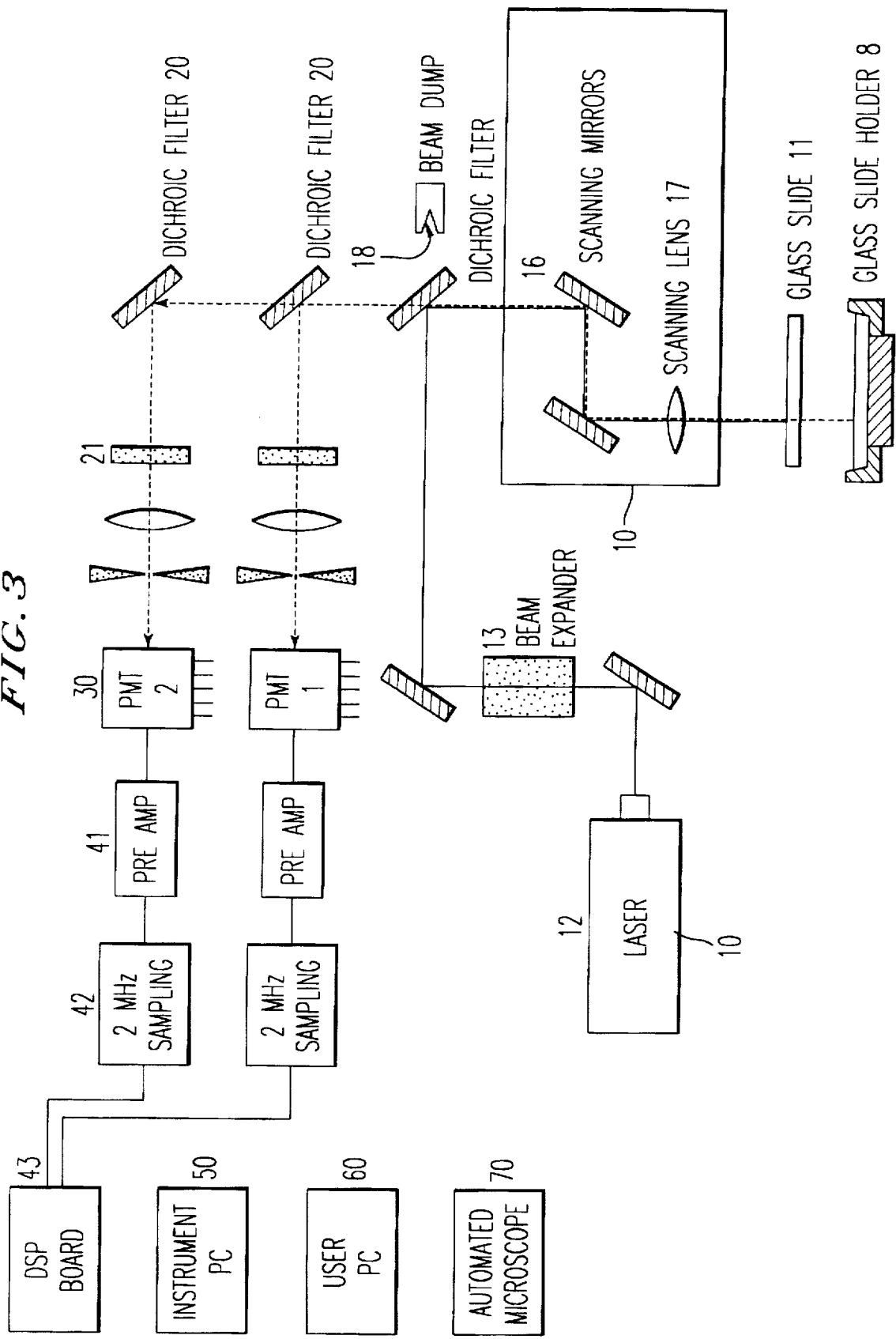
FIG. 3: sketch of the apparatus showing; the laser, optics, scanning mirrors, specimen holder, detectors, and a black box for post detection electronics.
Figure 4:
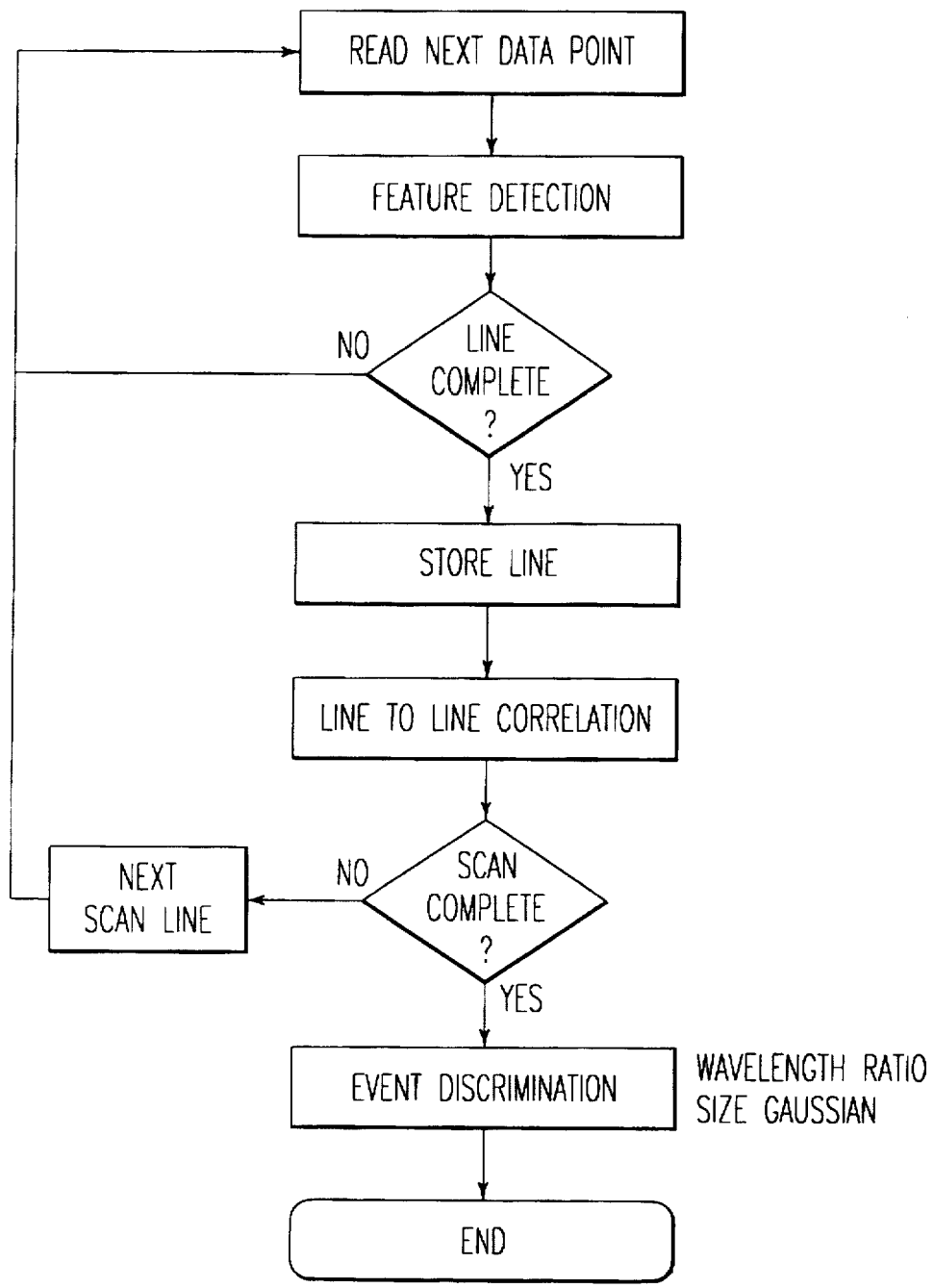
FIG. 4: flow chart showing top level control algorithm.
Figure 5:
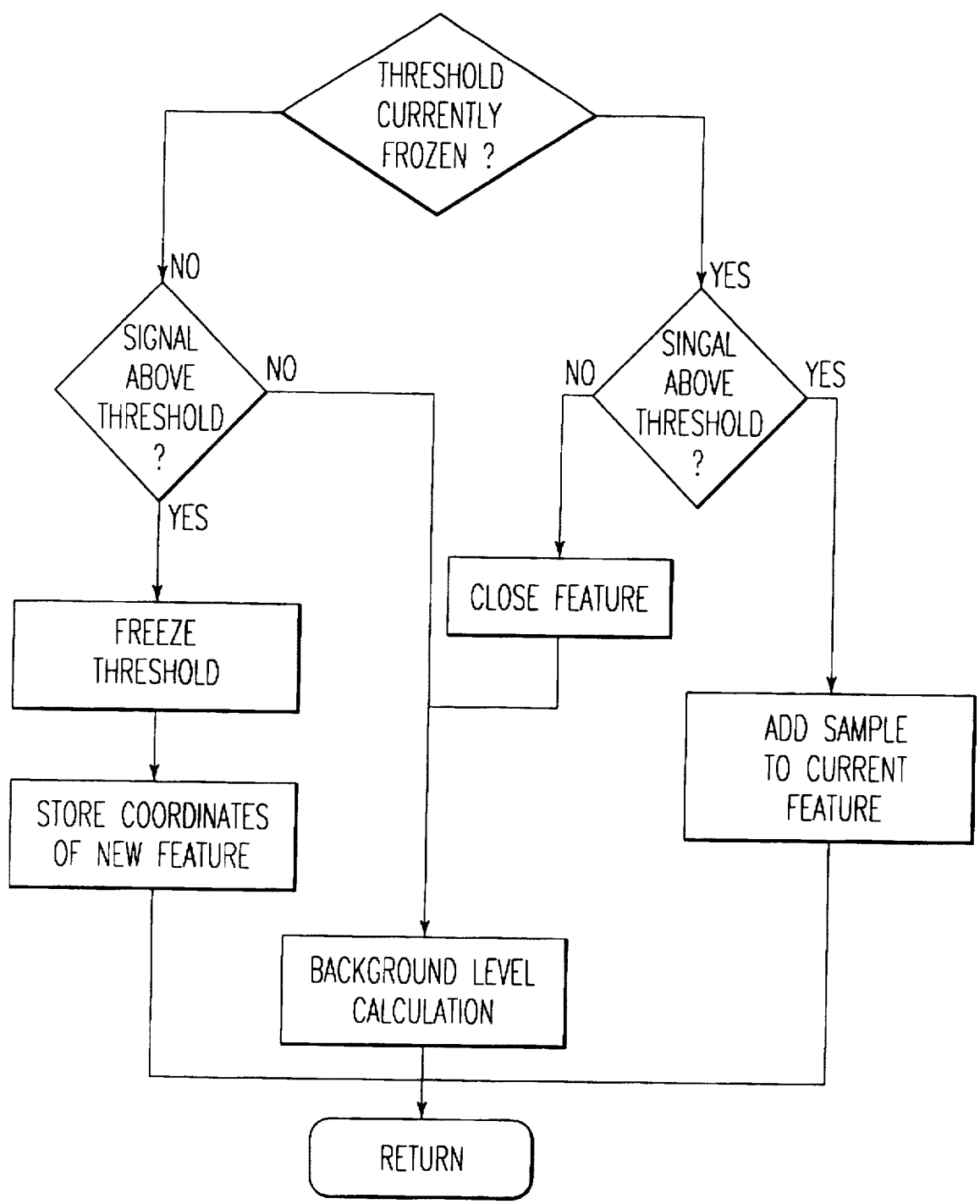
FIG. 5: flow chart showing feature detection.
Figure 6:
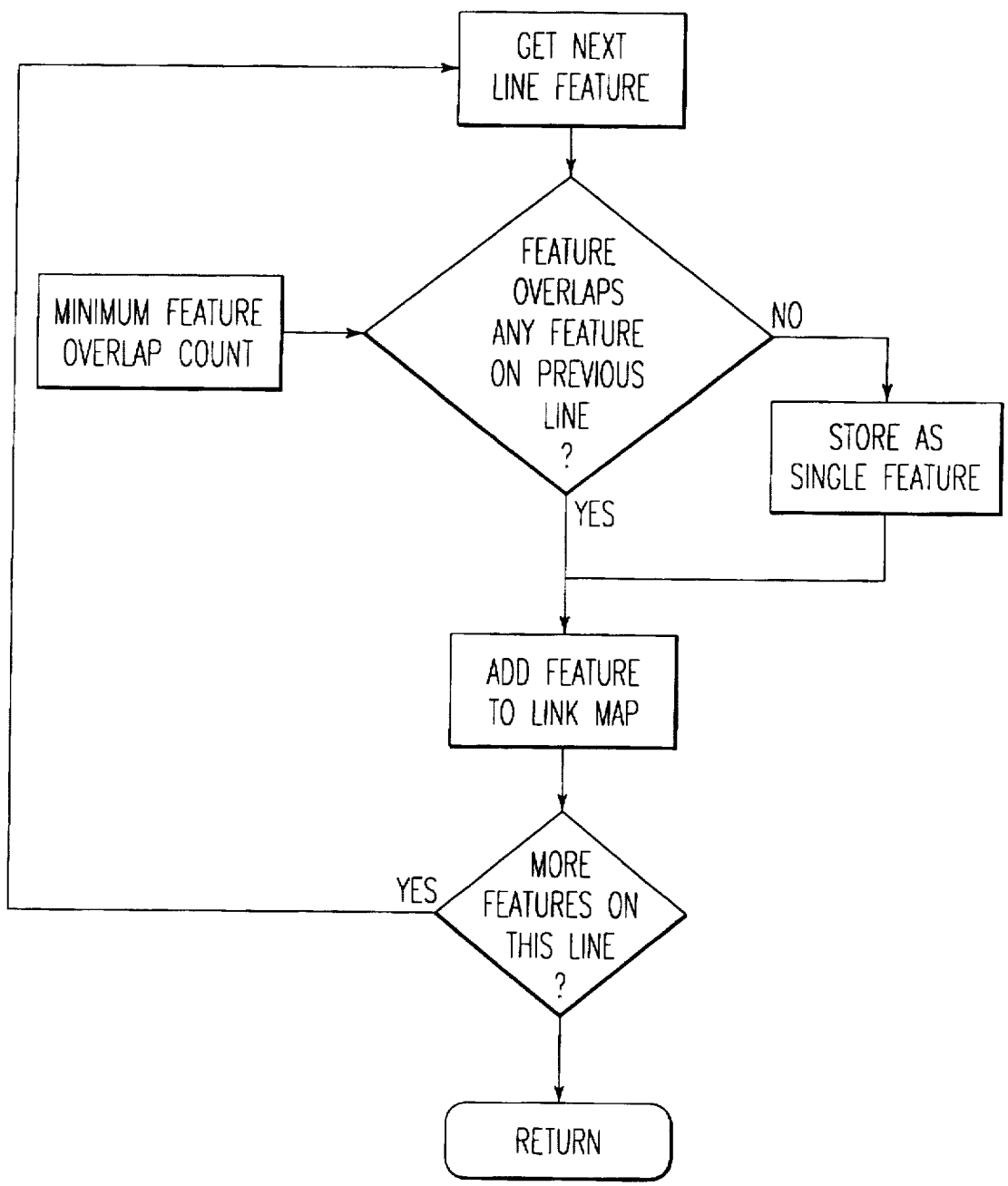
FIG. 6: flow chart showing line correlation.
Figure 7:
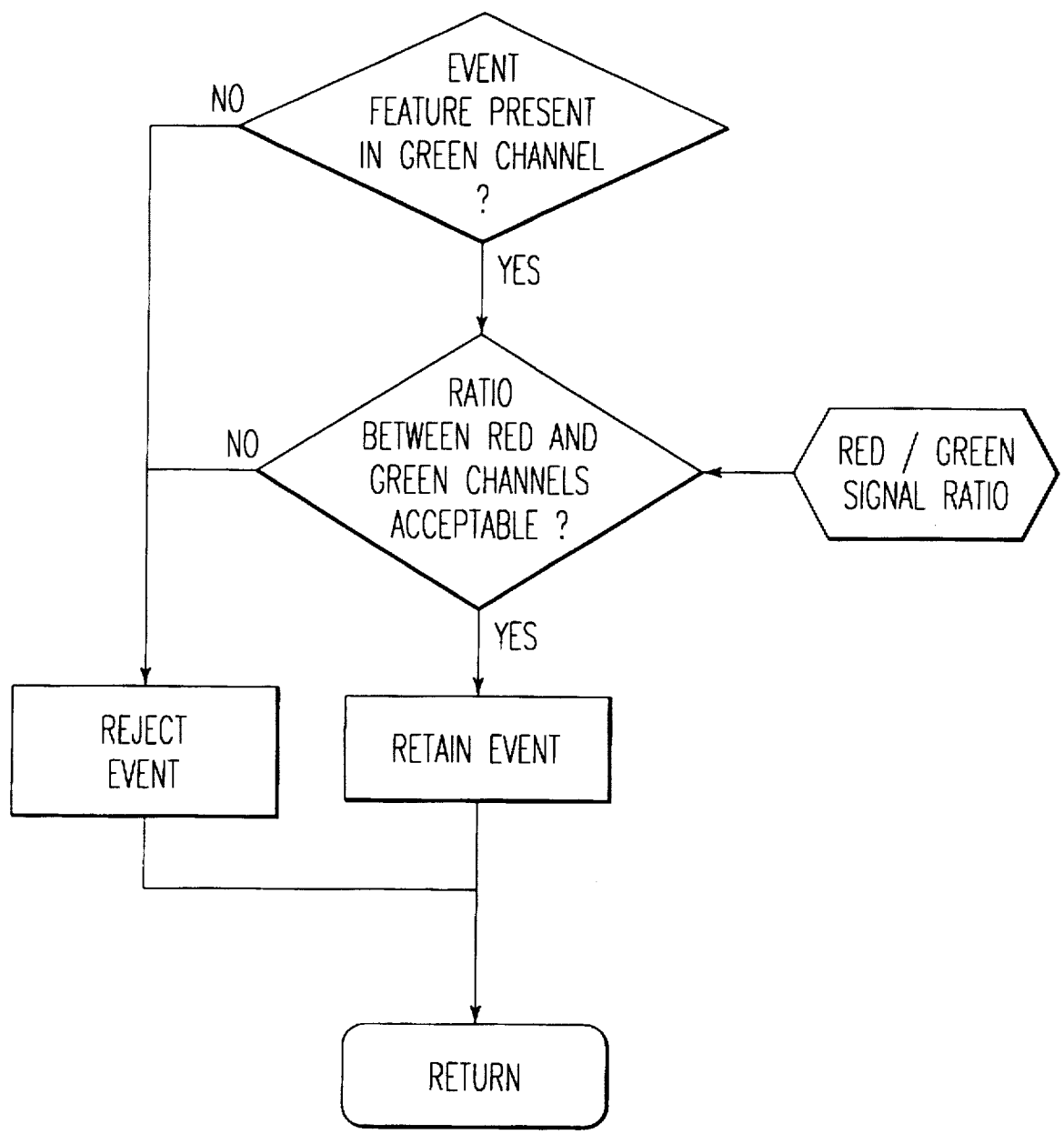
FIG. 7: flow chart showing color ratio discrimination.

Referring to FIG. 3, there is shown an apparatus according to the invention comprising scanning means 10, means for detecting the emitted fluorescence, including dichroic filters 20, optical filters, 21, photomultipliers (PMT) 30, a signal processing system 40–42, a digital signal processor 43, an instrument PC 50, a user PC 60 and an automated microscope 70.

The scanning device 10 uses coherent light to scan a solid support 11, represented by a glass slide, carried on a glass slide holder 8.

In the preferred embodiment, the components of the device 10 include: a 488 nm argon-ion water cooled laser 12, scan mirrors 16, scanning lens 17 and a beam dump 18 which is a safety feature; said scanning means cooperates with means for focusing said laser beam into a laser spot comprising a beam expander 13 which controls the illuminating laser spot size to 15–30 µm, preferably 20 µm, and directs the illuminating spot onto said scan mirrors 16.

Said beam expander 13 comprises two lenses, adapted (focal distance and distance between said two lenses), such as providing a laser spot on said solid support from 15 to 30 µm; for instance, to obtain a laser spot of 20 µm, focal distance of lens n.1 is 90 mm, focal distance of lens n.2 is 50 mm, and the distance between the two lenses is 36.5 mm.

Said two scanning mirrors are used to scan the illuminating laser spot across the solid support 11 on which is deposited the specimen containing the cells to be detected. The laser spot moves in the x direction at a speed for example of 1 meter per second.

Said scanning mirrors 16 (=scanner 16) allow, for instance, a line-to-line (y) spacing of 7 µm (distance between two scan lines).

High optical accuracy is required from said scanning means to ensure accurate positioning of the laser spot (scanning lens 17).

Using a laser spot size of 20 µm at a speed of 1 m/s, a 25 mm circle can be scanned in under 2 minutes.

The solid support 11 (or specimen support) (such as a glass slide) on which is deposited the specimen to be analyzed is placed on a removable specimen holder which is used to carry the specimen support from the laboratory, or from where ever the specimen is collected, and to introduce it into the machine.

This specimen holder is designed to handle preferably a rectangular specimen support, such as a glass slide.

The load drawer (not represented) is easily accessible to the user. The removable specimen holder is designed to handle a rectangular solid support and is deposited on the load drawer. The drawer is then pushed into the instrument and the specimen holder carrying the cells comes directly under the scanner 16. The specimen holder is cooled to protect the stability of the labelled cells (for instance by Peltier effect).

Said specimen loader cooperates with a mechanism to introduce the specimen holder in the machine and to automatically bring it with precision at the right distance from the scanning lenses. The specimen loader is not shown on the figures.

The scanner 16 passes the focused laser beam to the glass slide 11, thereby inducing fluorescence from the cells or any fluorescent material.

The thus fluorescent light emitted from the specimen glass slide passes through dichroic filters 20 and optical filters 21 to two photomultipliers (PMTs) 30.

Said PMTs 30 detect fluorescence at two wavelengths (centred on 530 nm and 615 nm and referred to as the green and the red channels).

Said fluorescence is further analyzed by the signal processing system 40.

The PMT signals, together with time synchrony information from the scanner 16, are passed to the signal processing system 40.

This system 40 comprises pre-amplifiers 41, signal sampling devices 42 and digital signal processing unit 43.

More precisely, each of said PMT signals is amplified by a dedicated preamplifier 41. The amplified analogue signals are digitized sampled at 2 MHz, using 8-bit resolution (256 signal levels). Each PMT channel has a dedicated digitizer.

The digitized PMT signals are passed to a Digital Signal Processor (DSP) 43.

The signals are then analyzed and the resulting output information is passed through an instrument PC 50, which controls the scanning device, acts as a host for the DSP system 43, stores data during solid support scanning and passes scan results to the user PC 60.

Said user PC system 60 is used to process and display the results of a scan, currently using Matlab® software, as the principal analytical tool.

The instant apparatus has the facility to allow, if necessary, direct observation of any object on the solid support, by driving an automated microscope from the user PC 60.

Figure 8:
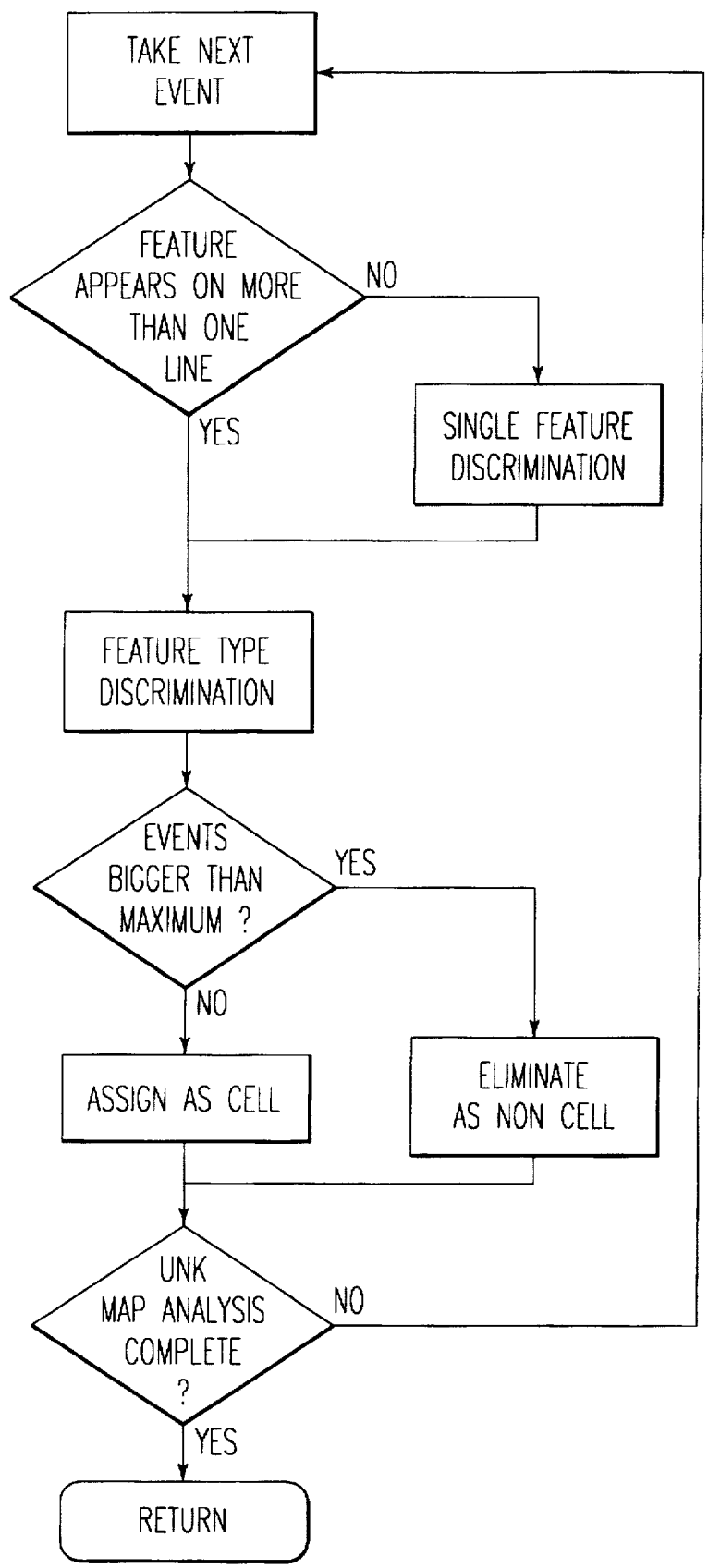
FIG. 8: flow chart showing event size discrimination.

FIGS. 4–8 sum up the different steps of the instant process in view to reject:

background noise (dynamic threshold, FIG. 5),
colour discrimination (FIG. 7),
uncorrelated features (FIG. 6),
size discrimination (FIG. 8).
Effect of variation on design parameters.

Figure 9:
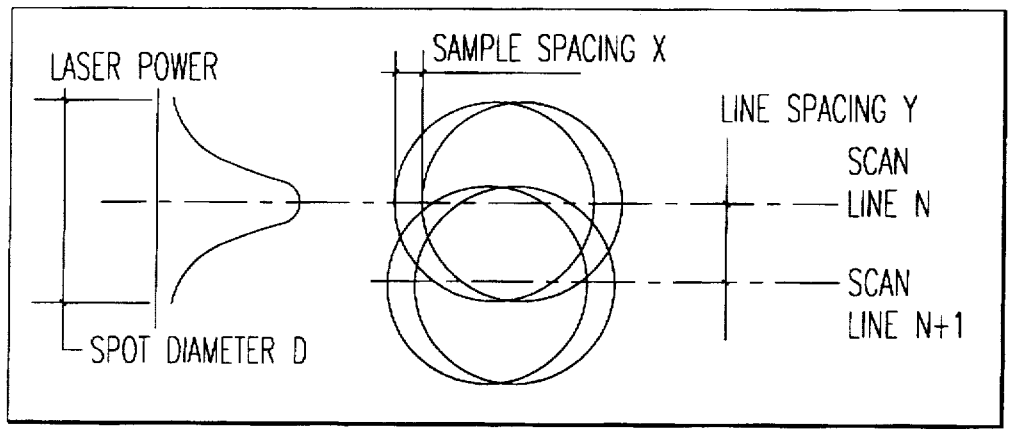
FIG. 9: illustrates the principal scanning paramaters d, x, y.

The following scanning physical parameters: laser spot size (d), scan line sampling (x) and line spacing (y) influence the detection performance of the instant process, as illustrated in FIG. 9. They are:

d: the scan laser spot dimension. The spot power distribution is Gaussian, and the spot dimension is usually defined as the dimension at which the laser intensity has fallen to ($1/e^2$) of the peak value (approximately 13%).

x: the distance between successive data samples on one scan line. This is controlled by the sampling rate, and the speed of the scanning mirrors.

y: the distance between successive scan lines. This is controlled by the step size used to move the scanning mirror.

The effect of varying these parameters is summarised in Table II. It is clear that there is an optimum operating region for each parameter. The size of this region is determined by three principal constraining factors:

minimising the probability of obtaining false positive or false negative result;

practical engineering constraints (component tolerances, scanning mirror positional accuracy, etc);

processing and data analysis system costs (process speed, data storage memory).

TABLE II

| Parameter | Current value | Requirement | Change | Issues and effect of change |
|---|---|---|---|---|
| Spot diameter | 20 μm | Small enough to discriminate two close events | Bigger spot smaller spot | False-negative due to lower signal level Increased scan time |

TABLE II-continued

| Parameter | Current value | Requirement | Change | Issues and effect of change |
|---|---|---|---|---|
| Line spacing y | 7 μm | small enough to see fluorescent cells on 2 consecutive lines | Larger spacing smaller spacing | False-negative if cell not seen on 2 lines mechanical tolerances; data storage; scan time |
| scan line sampling x | 0.5 μm (2 mHz) | Small enough to distinguish noise from real event | Higher spacing (lower sample rate) Lower spacing (high sample rate) | Insufficient discrimination Mechanical tolerances; data storage; scan time |

Figure 1:
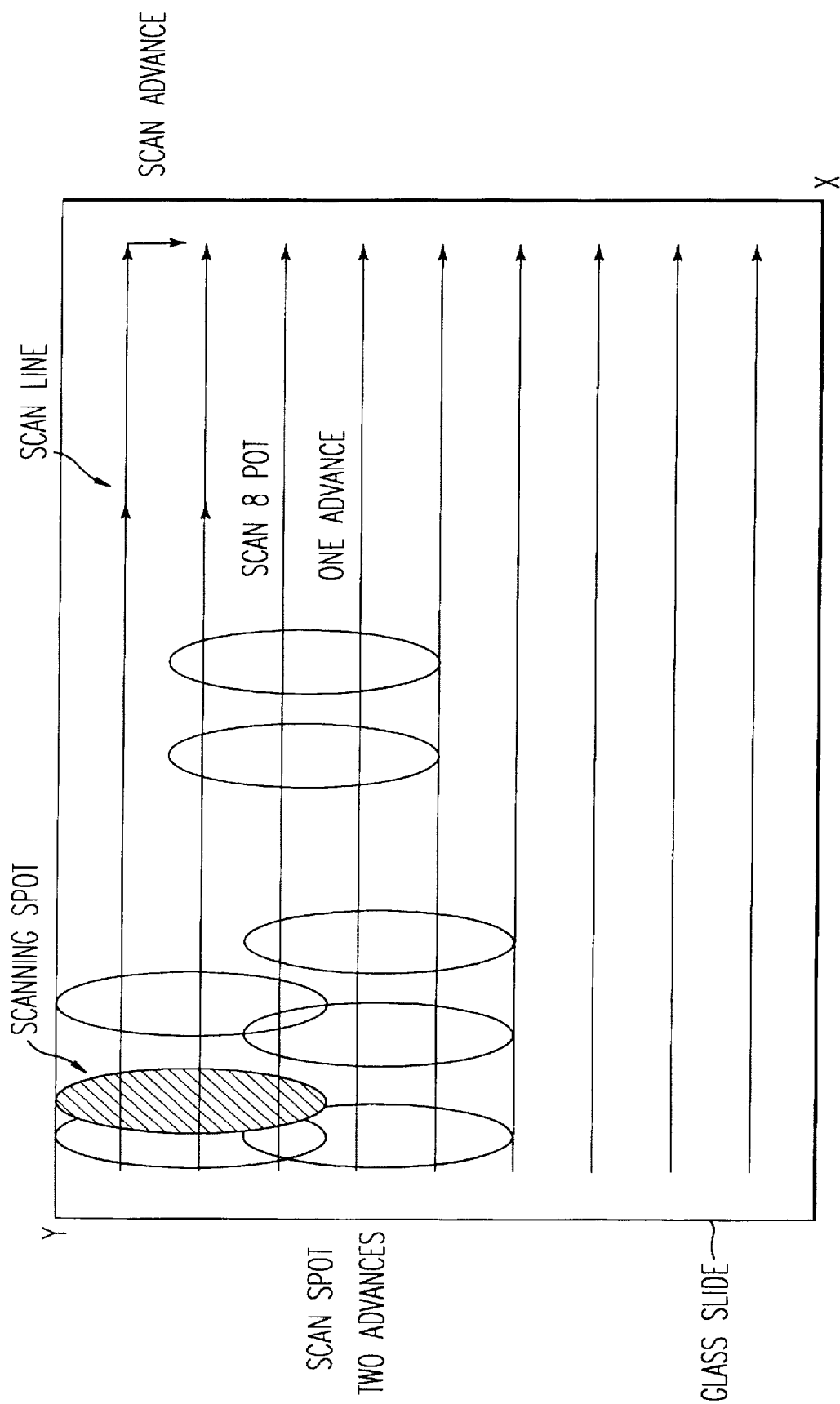
FIG. 1: drawing of overlapping scan pattern showing: beam shape, scan pattern, direction and relative dimensions.
Figure 2:
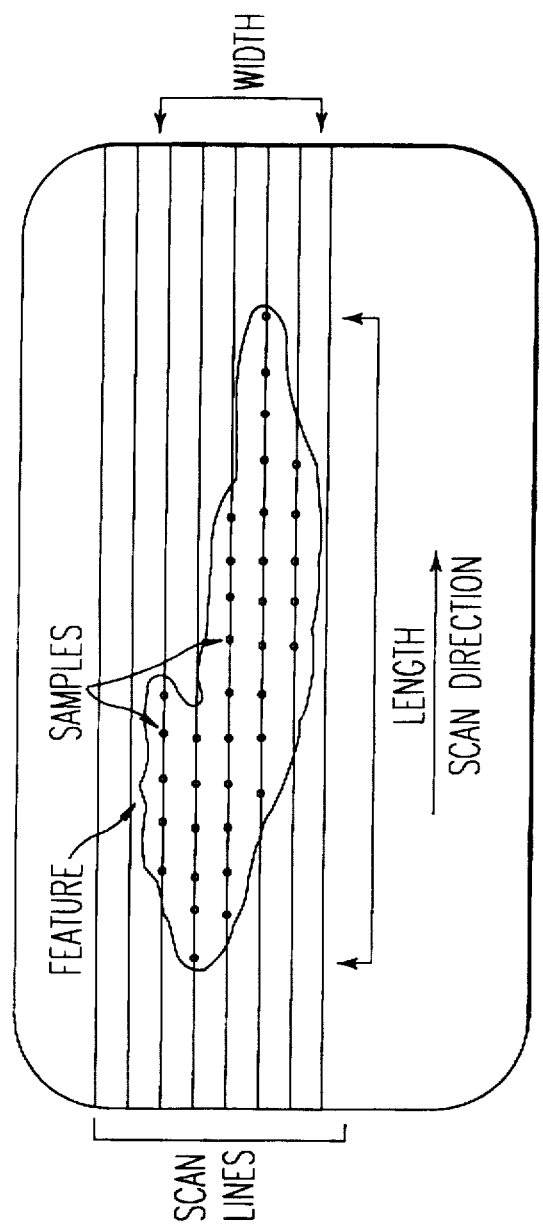
FIG. 2: definition and dimension of an event.
Figure 10:
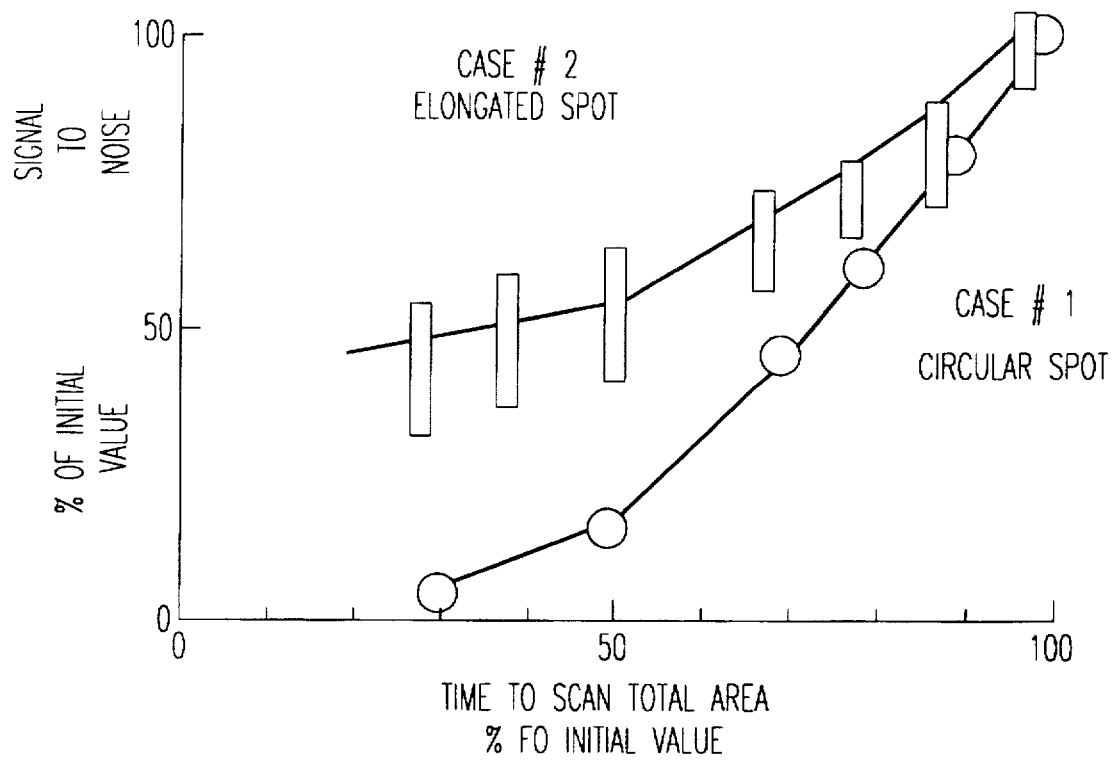
FIG. 10: illustrates a comparison of reduction in signal to noise when the laser spot is circular (Case 1) or elongated (Case 2).

The role of these parameters is also shown in FIGS. 1 and 10.

The target 11 is scanned as shown in FIG. 1. With reference to said FIG. 1, the scan time in terms of laser spot dimension and the SNR may be evaluated as follows:

total area scanned is X.Y scan velocity is v retrace time is negligible laser spot dimensions are $a_x$ and $a_y$ scan advance is Δy Then the time to scan the total area is equal to the time to scan one line times the number of scan lines.

Time per line=X/v

Number of lines =Y/Δy

Δy=$a_y$/n where n is the of number of times each point is scanned.

Thus, the time to scan is given by:

$$\text{Scan time} = \frac{X \cdot Yn}{v \cdot a_y}$$

If all things are equal the time to complete a scan is proportional to the area scanned and the number of times each element is scanned. It is inversely proportional to the velocity of scan and the dimension of the spot in the Y direction.

However, all things are not equal and if the scan time is reduced by either the simple expedient of increasing the spot size or the velocity the signal to noise will be compromised.

The signal is proportional to the intensity of illumination (watts/sq.cm.) and the time that each spot is illuminated. The noise is proportional to the square root of the illuminated area and inversely proportional to the scan velocity. Thus, considering that:

the target cell is smaller than the illuminating spot;

the total laser power is a constant (Io) and is spread over the illuminating spot;

the scan may be overlapped as described above where n is the number of times each point is scanned.

The signal to noise can be expressed in terms of familiar quantities:

$$S/N = \frac{Io}{a_x \cdot a_y} \sqrt{\frac{n}{a_y \cdot v}}$$

This demonstrates explicitly how the detection signal to noise is reduced as either the scan speed or laser spot dimension is increased. Even though this equation does not consider the recovery of signal to noise which will be gained by correlation of adjacent scan lines (see FIG. 1).

FIG. 10 shows a comparison of the results of the two equations developed above, under two sets of conditions. In each case, it was assumed that an initial condition existed with a circular laser spot of dimension a. Under this condition, the SNR was 100% and the scan time was 100%.

Condition 1: increase the laser spot dimension at constant velocity maintaining a circular spot and with no overlapping scan.

n=1 and $a_x=a_y$

Condition 2: elongate the spot by increasing the y dimension while decreasing the x dimension such that the spot area is constant and overlap so that each point is scanned twice:

n=1 and $a_x=1/a_y$

EXAMPLE 1

Detection of human cells (Hela cells) infected with the vaccinia virus

Cells ($10^5$/ml) were grown on slide and treated with wild type vaccinia virus at 2 $10^{-1}$ pfu/ml. Six hours after infection, cells were incubated 20 minutes with a FITC labelled vaccinia monoclonal antibody, then washed with PBS buffer; 20 µl of the treated suspension ($2.10^3$ cells) were deposited between slide and coverslip, and counted using the present invention. Parameters setting on the apparatus, basic detection results and final results after discrimination process are presented in the Table III. Detected cells were later confirmed positive under microscope.

EXAMPLE 2

Detection of murine transformed cells

A few β galactosidase protein constitutively expressing P13-1 cells, constructed from P-815 cells (murine plasmocytome) were added to a non-transfected cells suspension; the resulting suspension was labelled 5 minutes at 37° C. using fluorescein di-galactoside. After labelling, 30 µl were deposited between slide and coverslip and counted using the present invention. Parameters setting on the apparatus, basic detection results and final results after discrimination process are presented in Table III.

TABLE III

DETECTION AND COUNTING OF FLUORESCENT "RARE EVENTS" IN BIOLOGY AND MEDECINE

| Cells | PARAMETERS SETTING | | | | | BASIC DETECTION RESULTS Green Channel | | |
|---|---|---|---|---|---|---|---|---|
| | Laser power | Spot size | Green PMT (Volt) | Red PMT (Volt) | Ratio* greater than | Samples | Features | Events** |
| Infected Hella, cells | 50 mw | 14 µm | 680 | 750 | 0 | 12747 | 565 | 76 |
| β Gal + P13 − 1 | 60 mw | 14 | 650 | 750 | 0 | 3667 | 195 | 49 |

| Cells | BASIC DETECTION RESULTS Red Channel | | | NUMBER OF EVENTS ELIMINATED BY DISCRIMINATION PROCESS | | | FINAL RESULTS |
|---|---|---|---|---|---|---|---|
| | Samples | Features | Events** | Ratio | Single Feature | "size" | |
| Infected Hella, cells | 4694 | 215 | 19 | 9 | 33 | A > 45 B > 15 1 | 33 |
| β Gal + P13 − 1 | 1839 | 104 | 26 | 18 | 5 | A > 25 B < 5 0 | 24 |

It must be pointed out that in said Table III, "*Ratio" means fluorescent intensity in the red channel divided by fluorescent intensity in the green channel and the columns marked "●●" actually include the total of events as defined in the text and the number of uncorrelated features (also called single features). It is also to be noted that features and events may be found in the red channel only and vice versa and impact of discrimination by Gaussian after other criteria not shown on this Table.

We claim:

1. Method for detecting and counting rarely occurring mammalian cells, comprising the steps of:

scanning a solid support on which a specimen potentially containing fluorescent cells has been deposited, with an incident beam from a laser to thereby form a laser spot on the solid support, said laser spot being substantially greater than the cells to be detected, and said laser spot size being between 15 and 30 µm, wherein the distance between two scanning lines is such that each element of the said support is scanned at least twice, by partial overlapping of adjacent scanning paths; and simultaneously:

detecting the resultant fluorescent light at least at one wavelength, by selecting as samples only detected signals exceeding a given threshold, wherein a set of adjacent samples on a scan-line represents a feature;

establishing a set of correlated-features by a line-to-line correlation of individual features, by comparing features on each pair of adjacent lines in time synchrony, counting the number of lines over which said set of correlated-features occur, each set of correlated-features forming an event, and eliminating any single-uncorrelated-features;

comparing said correlated-features on each pair of adjacent lines in time synchrony, at least at two different wavelengths $\lambda_1$ and $\lambda_2$, for selecting the correlated-features having an emission intensity ratio at said two wavelengths lower than a predetermined number, being specified that if the emission ratio at said wavelengths generated by any correlated samples is greater than a predefined value, the complete event is eliminated;

making a size discrimination of retained events and selecting those having a size corresponding to the type of cells searched;

determining if for retained events after size discrimination, the events energy profile in three dimensions is within predetermined Gaussian shape criteria and rejecting events not within said predetermined Gaussian shape criteria; and counting said remaining events to determine and to count exclusively the fluorescent cells present on said solid support.

2. The method as in claim 1, wherein said size discrimination by comprises the steps of:

determining the length of each event by counting the number of samples, by starting with the sample appearing first on the scanning direction on whatever feature of said event occurring the earliest, continue to include the sample appearing last in the scan direction on whatever feature ends last, said counting taking as one sample all the correlated samples of different scan lines, determining the width of said event by counting the number of adjacent lines covered by the same event and eliminating events for which the number of said counted samples is greater than a predetermined number A, and/or the number of said adjacent scan-lines is greater than a predetermined number B.

3. Method for detecting and counting rarely occurring mammalian cells, comprising the steps of:

spreading the specimen to be analyzed and potentially containing the rare mammalian cells to be detected, over a solid support, in such a way to obtain a thin layer;

depositing on the solid support appropriate reagents to fluorescently label the cells searched using techniques which cause emission of a fluorescent light at a selected wavelength; such techniques being used either individually or simultaneously on a given sample to produce fluorescent light at one or more wavelength as a discrimination tool or as a way of identifying or selecting only certain type of rare cells;

scanning said solid support with an incident beam from a laser, forming a laser spot on said solid support, said laser spot being substantially greater than the cells to be detected, said laser spot size being comprised between 15 and 30 µm, wherein the distance between two scanning lines is such that each element of the said support is scanned at least twice, by partial overlapping of adjacent scanning paths; and simultaneously:

detecting the resultant fluorescent light at least at one wavelength, by selecting as samples only detected signals exceeding a given threshold, wherein a set of adjacent samples on a scan-line represents a feature;

establishing a set of correlated-features by a line-to-line correlation of individual features, by comparing features on each pair of adjacent lines in time-synchrony, counting the number of lines over which said set of correlated-features occur, each set of correlated-features forming an event, and eliminating any single uncorrelated-features;

comparing said correlated-features on each pair of adjacent lines in time synchrony, at least at two different wavelengths $\lambda_1$ and $\lambda_2$ for selecting the correlated-features having an emission intensity ratio at said two wavelengths lower than a predetermined number, being specified that if the emission ratio at said wavelengths generated by any correlated samples is greater than a predefined value, the complete event is eliminated;

making a size discrimination of retained events and selecting those having a size corresponding to the type of cells searched;

determining if, for retained events after size discrimination, the events energy profile in three dimensions is within predetermined Gaussian shape criteria and rejecting events not within said predetermined Gaussian shape criteria; and counting said remaining events to determine and to count exclusively the fluorescent cells present on said solid support.

4. The method as in claim 3, wherein said size discrimination comprises the steps of:

determining the length of each event by counting the number of samples, by starting with the sample appearing first on the scanning direction on whatever feature of said event occurring the earliest, continue to include the sample appearing last in the scan direction on whatever feature ends last, said counting taking as one sample all the correlated samples on different scan lines, determining the width of said event by counting the number of adjacent lines covered by the sane event and eliminating events for which the number of said counted samples is greater than a predetermined number A, and/or the number of said adjacent scan-lines is greater than a predetermined number B.

5. Apparatus for detecting and counting cells by fluorescence, comprising:

a laser light source for emitting an incident light beam, cooperating with means for focusing said laser beam into a laser spot, the dimension of which on a solid support is substantially greater than the type of mammalian cells to be detected and counted, said laser spot size being comprised between 15 and 30 µm;

scanning means for directing the light from said light source onto said solid support to spotwise irradiate the mammalian cells to produce fluorescence spots, wherein the distance between two scanning lines is such that each element of the support is scanned at least twice, by partial overlapping of adjacent scanning paths;

means for detecting and photoelectrically converting said emitted fluorescence at least at two different wavelengths $\lambda_1$ and $\lambda_2$;

means for discriminating and eliminating non-mammalian fluorescence including a digital signal processor and a plurality of optic paths for selecting at least two emission fluorescence wavelengths;

signal processing means for establishing sets of correlated-features by a line-to-line correlation of individual features, by comparing features on each pair of adjacent lines in time synchrony, counting the number of lines over which said set of correlated-features occur, each set of correlated-features forming an event, and eliminating any single uncorrelated feature, occuring only on one line; comparing said correlated-features on each pair of adjacent lines in time synchrony, at least at two different wavelengths $\lambda_1$ and $\lambda_2$, for selecting the correlated-features having an emission intensity ratio at said two wavelengths lower than a predetermined number, being specified that if the emission ratio at said wavelengths generated by any correlated features is greater than a predefined value, the complete event is eliminated; making a size discrimination of retained events and selecting the events having a size corresponding to the type of mammalian cells searched; determining if for retained events after size discrimination, the events energy profile in three dimensions is within predetermined Gaussian shape criteria and rejecting events not within said predetermined Gaussian shape criteria, and counting said remaining events to determine and to count exclusively the fluorescent mammalian cells present on said solid support.

6. Apparatus as in claim 5, characterized in that said scanning means comprises a first oscillating mirror, the axis of oscillation of which is perpendicular to the axis of the light beam for scanning a line by the beam; and a second mirror, the axis of which is perpendicular to the axis of oscillation of the first mirror, said second mirror executing a scanning movement synchronized with the scanning movement of said first mirror.

7. Apparatus as in claim 5, characterized in that said detecting means includes at least two photo-multipliers as a means for the photoelectric conversion.

8. Apparatus as in claim 5, characterized in that said laser spot has an elongated shape.

9. Apparatus as in claim 5, characterized in that said solid support is a glass slide.

10. Apparatus as in claim 5, characterized in that said solid support is placed on a sample holder cooperating with cooling means and optionally a thin layer of silicon material sandwiched between said sample holder and said solid support.

* * * * *

UNITED STATES PATENT AND TRADEMARK OFFICE
CERTIFICATE OF CORRECTION

PATENT NO. : 5,751,839
DATED : MAY 12, 1998
INVENTOR(S) : Jean-Louis DROCOURT et al.

It is certified that error appears in the above-identified patent and that said Letters Patent is hereby corrected as shown below:

In column 2, line 1, change "anormal" to --abnormal--.

In column 8, line 44, change "$80_2$" to --$\lambda_2$--.

Signed and Sealed this

Eighteenth Day of May, 1999

Attest:

Attesting Officer

Q. TODD DICKINSON

Acting Commissioner of Patents and Trademarks